(12) United States Patent
Philippe et al.

(10) Patent No.: US 6,521,222 B1
(45) Date of Patent: Feb. 18, 2003

(54) INORGANIC/ORGANIC COMPLEXES FOR REDUCING SKIN IRRITATION

(75) Inventors: Michel Philippe, Wissous (FR); Catherine Cohen, Paris (FR)

(73) Assignee: Societe L'Oreal S.A., Paris (FR)

( * ) Notice: Subject to any disclaimer, the term of this patent is extended or adjusted under 35 U.S.C. 154(b) by 0 days.

(21) Appl. No.: 09/671,627

(22) Filed: Sep. 28, 2000

(30) Foreign Application Priority Data

Sep. 28, 1999 (FR) .............................................. 99 12057

(51) Int. Cl.⁷ .......................... A61K 31/74; A61K 6/00; A61K 7/00; A61K 31/28; A61K 31/12; A01N 55/02; A01N 35/00

(52) U.S. Cl. ................. 424/78.03; 424/401; 424/78.05; 514/492; 514/675; 514/844; 514/887

(58) Field of Search ........................... 424/401, 43, 59, 424/65, 70.1, 78.03, 78.05, 78.06; 514/159, 499, 675, 715, 723, 844, 861, 863, 887

(56) References Cited

U.S. PATENT DOCUMENTS

| | | | | |
|---|---|---|---|---|
| 4,322,441 A | * | 3/1982 | Engel et al. ................. | 514/675 |
| 5,372,850 A | * | 12/1994 | Uchikawa et al. ...... | 427/255.31 |
| 5,583,242 A | * | 12/1996 | Schieven ...................... | 556/44 |
| 5,716,625 A | * | 2/1998 | Hahn et al. .................. | 424/401 |
| 5,820,664 A | * | 10/1998 | Gardiner et al. ........ | 106/287.17 |
| 5,958,436 A | * | 9/1999 | Hahn et al. .................. | 424/401 |
| 6,033,677 A | * | 3/2000 | Cabane et al. .............. | 424/401 |
| 6,126,996 A | * | 10/2000 | Kirlin et al. ................. | 427/252 |
| 6,166,078 A | * | 12/2000 | Cantin et al. ................ | 514/557 |

FOREIGN PATENT DOCUMENTS

GB 901554 3/1960

* cited by examiner

Primary Examiner—Sreeni Padmanabhan
Assistant Examiner—Lauren Q. Wells
(74) Attorney, Agent, or Firm—Burns, Doane, Swecker & Mathis, L.L.P.

(57) ABSTRACT

β-Diketone/hydroxylated or carbonated activated cation inorganic/organic complexes are well suited for reducing skin irritation, notably that elicited by exposure to irritant active agents/species or to the external environment.

23 Claims, No Drawings

INORGANIC/ORGANIC COMPLEXES FOR REDUCING SKIN IRRITATION

CROSS-REFERENCE TO PRIORITY APPLICATION

This application claims priority under 35 U.S.C. §119 of FR-99/12057, filed Sep. 28, 1999, hereby expressly incorporated by reference.

BACKGROUND OF THE INVENTION

1. Technical Field of the Invention

The present invention relates to a method or regime/regimen for reducing skin irritation, notably that irritation attributed to the topical application of certain active species onto the skin, or due to exposure to the environment.

This invention especially relates to reducing skin irritation by treating the skin with effective amounts of certain inorganic/organic complexes, or compositions comprised thereof.

2. Description of the Prior Art

A wide variety of compounds are formulated into cosmetics to, inter alia, improve the appearance of the skin, to beautify the skin, to treat skin conditions, or to render the skin less dry or more supple. Unfortunately, certain of these compounds may cause irritation when they are topically applied onto the skin or mucous membranes.

It is known to this art to administer salicylic acid derivatives as keratolytic agents for treating acne; these are also useful anti-aging agents in cosmetic and/or dermatological compositions. Thus, FR-A-2,581,542 and EP-A-378,936 describe such salicylic acid compounds.

Salicylic acid derivatives are of great value, given their biological effects on the skin, in particular on the principal clinical signs of skin aging, namely, fine lines and wrinkles, disorganization of the "grain" of the skin, modification of the skin's complexion and loss of skin firmness and tonicity. However, administration of these derivatives presents a problem since they can cause stinging, itching and tautness after they have been applied, which may result in considerable discomfort. Users, and more particularly those having sensitive skin, are thus often discouraged from using these compounds. Sensitive skin and the signs which are characteristic of sensitive skin are described in EP-680,749.

The same also holds true for exfoliants such as hydroxy acids. Concerning these compounds, it has been proposed, in EP-413,528, to combine them with amphoteric species in order to decrease the discomfort that they may cause.

It is also widely described that some users of cosmetic products comprising surfactants, preservatives, fragrances, solvents or propellants complain that their skin is irritated after applying one or more of the above substrates thereto.

However, because of their irritant nature, these products are generally employed at very low doses. Formulation of these products in small amounts may, therefore, prove to be relatively disadvantageous with respect to administration of other active species which are less active, but which are formulated in greater amounts since they are less or not irritant.

It is also known to this art that the skin of certain individuals is irritated when it has been exposed to a specific or unusual chemical or physical environment, in particular when it is exposed to considerable variations in temperature, to wind or to a very polluted environment. Thus, the skin may react with itching, tautness or stinging.

Thus, the irritation may be characterized by stinging, itching or tautness, which too may cause considerable discomfort.

WO-A-96/19184, WO-A-96/19182 and WO-A-96/19228 describe the administration of water-soluble divalent strontium, manganese, magnesium and calcium salts to reduce the irritation of compounds which have an irritant effect, in particular of exfoliants such as hydroxy acids.

SUMMARY OF THE INVENTION

It has now unexpectedly and surprisingly been determined that certain inorganic/organic complexes are useful for reducing the irritation induced, in particular, by certain species or products topically applied onto the skin, or by exposure to the environment.

Briefly, the present invention features therapeutically/cosmetically treating skin irritation by topical application onto the afflicted skin of at least one compound having the formula (I):

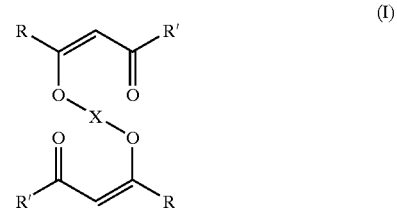

in which the radicals R, which may be identical or different, are each a linear or branched, saturated or unsaturated, optionally hydroxylated alkyl or perfluoroalkyl radical having from 1 to 12 carbon atoms; the radicals R', which may be identical or different, are each a linear or branched, saturated or unsaturated, optionally hydroxylated alkyl, alkyloxy or perfluoroalkyl radical having from 1 to 12 carbon atoms; and X is an element selected from among magnesium, strontium, barium, zinc, manganese, palladium or copper.

The subject compounds of formula (I) are either in hydrated or nonhydrated state and, advantageously, constitute organic/inorganic complexes.

The present invention thus also features a cosmetic method or regime/regimen comprising topically applying onto the skin, the keratin fibers, the nails, or the mucous membranes, at least one compound of formula (I) or composition comprised thereof.

Too, this invention features formulating at least one compound of formula (I):

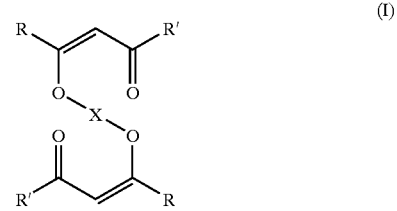

in which the radicals R, which may be identical or different, are each a linear or branched, saturated or unsaturated, optionally hydroxylated alkyl or perfluoroalkyl radical having from 1 to 12 carbon atoms; the radicals R', which may be identical or different, are each a linear or branched, saturated or unsaturated, optionally hydroxylated alkyl, alkyloxy or perfluoroalkyl radical having from 1 to 12 carbon atoms; and X is an element of column IIA of the Periodic Table (CAS version), zinc, manganese, palladium or copper, whether hydrated or nonhydrated, into a topically applicable, physiologically acceptable medium (vehicle, diluent or carrier) and thus producing a dermatological or pharmaceutical composition, effective as an agent which reduces skin irritation.

The subject compounds/compositions are particularly useful soothing agents and can be formulated as cosmetic products.

DETAILED DESCRIPTION OF BEST MODE AND SPECIFIC/PREFERRED EMBODIMENTS OF THE INVENTION

More particularly, according to the present invention, by "linear or branched alkyl radical having from 1 to 12 carbon atoms" are especially intended methyl, ethyl, propyl, isopropyl, butyl, tert-butyl, hexyl, 2-ethylhexyl, octyl, nonyl, dodecyl, 2-methylbutyl, 2-methylpentyl, 1-methylhexyl and 3-methylheptyl radicals.

Preferably, R is a linear or branched, saturated alkyl or perfluoroalkyl radical having from 1 to 6 carbon atoms. In addition, R' is advantageously a linear or branched, saturated alkyl, alkyloxy or perfluoroalkyl radical having from 1 to 6 carbon atoms.

Preferably, the substituents R and R' are linear and/or saturated.

In particular, the substituents R and R' preferably comprise a difference of at most two carbon atoms with respect to each other.

These compounds of formula (I) are water-insoluble, unlike the compounds described in WO-A-96/19184, WO-A-96/19182 and WO-A-96/19228. Their property of reducing the irritation which is, in particular, induced by certain products applied onto the skin, which are generally hydrophilic, such as hydroxy acids, is thus all the more surprising.

Exemplary derivatives according to the invention include strontium 2,4-pentanedionate, bis(1,1,1,2,2,3,3-heptafluoro-7,7-dimethyl-4,6-octanedionato)strontium hydrate, bis(2,2,6,6-tetramethyl-3,5-heptanedionato)strontium hydrate, strontium hexafluoroacetylacetonate, calcium 2,4-pentanedionate, bis(1,1,1,2,2,3,3-heptafluoro-7,7-dimethyl-4,6-octanedionato)calcium, calcium hexafluoroacetylacetonate dihydrate, calcium 2,2,6,6-tetramethyl-3,5-heptanedionate, and mixtures thereof.

Certain of these compounds have been described as catalysts of chemical reactions or as reagents of methods for obtaining inorganic compounds, such as superconductors (WO 91/13051 or "Preparation and properties of beta-diketone and beta-keto ester complexes of bismuth (III), strontium (II) and calcium (II)" by Doi Masura et al., in *Nippon Kagaku Kaishi* (1995), (10), 802–8).

Preferably, the substituents R and R' are methyl radicals.

Advantageously, X is selected from among strontium, calcium, magnesium, manganese, barium, copper, zinc and palladium, and more especially is selected from among strontium, calcium, copper and zinc.

The compositions according to the invention are well suited for topical application onto the skin, keratin fibers, nails or mucous membranes; in particular, the subject compositions are cosmetic and/or dermatological compositions.

By the expression "physiologically acceptable medium" is intended a medium which is compatible with the skin, mucous membranes (including the inside of the eyelids and the lips), nails and/or keratin fibers (head hair and/or body hairs). In addition, this physiologically acceptable medium contains no reaction by-product or residual product, since the compounds of formula (I) are the result of a clean synthesis technique.

Specifically, these compounds are prepared via a method employing a carbonated or hydroxylated activated cation which will react with a β-diketone (the starting organic compound). The reaction by-products formed during the reaction are carbon dioxide or water, and they are eliminated from the reaction medium, in particular, in the form of gas or are easily eliminated after reaction (in particular with the washing water). Furthermore, if these reaction by-products remain present in trace amounts, they are nontoxic and/or nonreactive with respect to the compounds of formula (I).

Thus, the present invention also features compositions in which the compound of formula (I) is the result of the reaction between a β-diketone and a hydroxylated or carbonated activated cation.

The compounds of formula (I) according to the invention are advantageously present in an effective amount to ensure the desired result, i.e., to reduce or eliminate the irritation. They can be, for example, present in a composition according to the invention in a weight amount advantageously ranging from 0.001% to 30%, preferably from 0.01% to 20% and more preferably from 0.1% to 10%, of the total weight of the composition.

The compositions containing a compound according to the invention can be in any pharmaceutical form normally employed, and, in particular, one which is suitable for topical application, for example in the form of an oily solution, an oily gel, a liquid, pasty or solid anhydrous product, an emulsion of the water-in-oil (W/O), oil-in-water (O/W) or multiple (W/O/W or O/W/O) type, a microemulsion or a vesicle dispersion of ionic and/or nonionic type. These compositions are formulated according to the usual techniques.

As indicated above, the compounds of formula (I) are more particularly in the fatty phase of the compositions according to the invention.

These compositions can be more or less fluid and can have the appearance of a white or colored cream, an ointment, a milk, a lotion, a serum, a paste or a mousse. They can optionally be applied onto the skin in the form of an aerosol. They can also be in solid form and, for example, in stick form.

The subject compositions can also comprise at least one additive or adjuvant selected from among water, fatty substances, preservatives, gelling agents, surfactants and emulsifiers, antioxidants, fillers, solvents, fragrances, dyestuffs, and colorants, UV-screening agents, cosmetic and/or dermatological active agents such as moisturizers, vitamins and anti-aging active agents, and mixtures thereof. The amounts of these various additives and adjuvants are those conventionally used in the cosmetic and/or dermatological field.

The fatty substances can be selected from among synthetic oils, oils of animal origin, oils of plant origin, mineral oils (liquid petroleum jelly), silicone oils, fluoro oils, and mixtures thereof. Fatty alcohols, fatty acids and waxes can also be used.

When the composition formulated as an emulsion, the proportion of the fatty phase can range from 5% to 80% by weight, and preferably from 5% to 50% by weight, relative to the total weight of the composition. The oils, waxes, emulsifiers and co-emulsifiers included in the composition in emulsion form are selected from among those conventional in the cosmetic field. The emulsifier and the co-emulsifier are advantageously present in the composition in a proportion ranging from 0.3% to 30% by weight, and preferably from 0.5% to 20% by weight, relative to the total weight of the composition.

When the composition is an oily gel or solution, the fatty phase can represent more than 90% of the total weight of the composition.

Representative emulsifiers according to the invention include, for example, polyethylene glycol oleyl ethers such as the products marketed under the trademarks BRIJ92 and BRIJ96 by ICI.

The amounts of the various constituents of the compositions according to the invention are those conventional in the fields under consideration. The nature of the additives and adjuvants and their amounts should be such that they do not modify the properties of the compounds of formula (I) according to the invention.

The compositions of the invention can be used as cleansing, protective, treatment or care products and/or as makeup products for facial and/or body skin, mucous membranes and/or keratin fibers. They in particular constitute treatment or care creams for the face, for the hands or for the body (for example day creams, night creams, antisun or sunscreen creams), protective or care body milks, lotions (cleansing lotions, antisun or sunscreen lotions), skincare mousses or gels, or bath compositions. They can also constitute makeup products, in particular, for the cheeks, the lips, the eyelashes and the eyelids, such as foundations, lipsticks and eyeshadows: to this end, they can contain dyestuffs and in particular chemical dyes or pigments.

They can also be used for the hair in the form of solutions, creams, gels, emulsions or mousses, and in particular as haircare compositions such as shampoos, treating lotions, restructuring lotions for the hair, lotions or gels for combating hair loss, antiparasitic shampoos, etc.

The compositions according to the invention can also be formulated as solid preparations constituting cleansing bars or soaps.

The compositions comprising the compound of formula (I) can also comprise the product or active agent/species which can cause an irritation of the skin.

In this instance, the present invention also features compositions, preferably cosmetic, which comprise, formulated into a physiologically acceptable medium, at least one compound of formula (I) and at least one product which can cause an irritation of the skin.

The amount of the at least one compound of formula (I) according to the invention is preferably a sufficient amount such that the skin irritant effect decreases, or even disappears. Thus, this amount can be varied in particular as a function of the amount and of the nature of the product with an irritant nature which is applied. However, by way of illustration, and as indicated above, a composition according to the invention can comprise at least one compound of formula (I) at an amount ranging from 0.001% to 30%, preferably from 0.01% to 20% and more preferably still from 0.1% to 10%, of the total weight of the composition.

In the compositions according to the invention, the amount of the product which can cause an irritation of the skin can thus correspond to an amount which is sufficient to cause an irritation of the skin if it is present alone (without the compound of formula (I)).

The present invention presents, indeed, the advantage of being able to increase the amount of active agents, which are conventionally of irritant nature, in compositions with respect to the amount normally employed, with a view to improved effectiveness of the latter. Thus, the amount of active agent which can be used in the composition advantageously ranges from 5% to 50% of the total weight of the composition. In particular, it is possible to formulate hydroxy acids at up to 50% of the total weight of the composition, salicylic acid or derivatives thereof at up to 10%, or retinoids at up to 5%, without any discomfort for the user.

Many topically applied products have an irritant nature, especially for individuals (users) with skin which is easily irritated. Thus, these products, as described above, cause stinging, itching or tautness, which result in discomfort to the user which discourages further use.

The products which can cause an irritation of the skin are typically preservatives, surfactants, fragrances, solvents, propellants and active agents, and mixtures thereof.

Thus, even the products which are considered to be inert in a cosmetic composition can have an irritant nature when they are applied to the skin, the scalp, the nails or the mucous membranes, such as, in particular, preservatives, surfactants, fragrances, solvents or propellants.

Too, products considered as active agents in cosmetic compositions can have an irritant nature when they are applied to the skin, the scalp, the nails or the mucous membranes. This can be referred to as an irritant side effect exhibited by these products, which are, in particular, active agents such as, especially, certain sunscreens, hydroxy acids, in particular α-hydroxy acids (glycolic, lactic, malic, citric, tartaric, mandelic, etc.) and β-hydroxy acids, especially salicylic acid and its derivatives, keto acids, in particular in α- and β-form, derivatives of hydroxy or keto acids, especially in α- and β-form, retinoids (retinol and its esters, retinal, retinoic acid and its derivatives, retinoids, in particular those described in FR-A-2,570,377, EP-A-199,636, EP-A-325,540 and EP-A-402,072), anthralins (dioxyanthranol), anthranoids (for example those described in EP-A-319,028), peroxides (in particular benzoyl peroxide), minoxidil and its derivatives, lithium salts, antiproliferating agents such as 5-fluorouracil or methotrexate, certain vitamins such as vitamin D and its derivatives and vitamin B9 and its derivatives, hair tints or dyes (paraphenylenediamine and its derivatives, aminophenols), perfuming alcoholic solutions (fragrances, eaux de toilette, aftershave and deodorants), antiperspirants (some aluminum salts), hair-removing or permanent-waving active agents (thiols), depigmenting agents (hydroquinone), capsaicin, antilouse active agents (pyrethrin), ionic and nonionic detergent agents and propigmenting agents (dihydroxyacetone, psoralens and methylangecilins), and mixtures thereof.

Among vitamin D and derivatives thereof, particularly exemplary as vitamin $D_3$, vitamin $D_2$, 1,25-dihydroxy vitamin $D_3$ (calcitriol), calcipotriol, 1,24-dihydroxy vitamin $D_3$ (such as tacalcitol), 24,25-dihydroxy vitamin $D_3$, 1-hydroxy vitamin $D_2$ and 1,24-dihydroxy vitamin $D_2$.

Among the salicylic acid derivatives, particularly exemplary are 5-n-octanoylsalicylic acid and 5-n-dodecanoylsalicylic acid, and their salts and esters thereof.

The present invention also features administering at least one compound of formula (I) formulated into a nonirritant cosmetic composition or a cosmetic composition suited for individuals with sensitive skin.

The compositions which comprise at least one compound of formula (I) and at least one active agent which causes irritation of the skin are particularly suitable for caring for and/or for treating and/or making up human skin and/or mucous membranes and/or keratin fibers, and in particular for combating the signs of aging of the skin and/or for improving the radiance of the complexion and/or for smoothing facial and/or body skin and/or for treating and reducing wrinkles and fine lines on the skin and/or for stimulating the process of epidermal renewal and/or for treating acne and/or for treating skin conditions/afflications.

Thus, this invention features the use of at least one compound of formula (I) in a cosmetic composition containing an active agent which causes irritation of the skin, destined for caring for human skin and/or mucous membranes and/or keratin fibers, and, in particular, intended for improving the radiance of the complexion and/or smoothing facial and/or body skin and/or combating the signs of aging of the skin and/or acne.

In addition, this invention features the manufacture or production of a dermatological or therapeutic composition containing at least one compound of formula (I) and an active agent which causes irritation of the skin and which is suited for combating the signs of aging of the skin and/or treating and reducing wrinkles and fine lines on the skin and/or stimulating the process of epidermal renewal and/or treating acne and/or skin conditions.

By the term "skin conditions" are intended, in particular, shingles, burns, eczema, demodectic acariasis, skin ulcers, fibrosis, controlling healing, psoriasis, pruritus, dermatitis, ichthyosis, corns and verrucae.

In order to further illustrate the present invention and the advantages thereof, the following specific examples are given, it being understood that same are intended only as illustrative and in nowise limitative.

In said examples to follow, all parts and percentages are given by weight, unless otherwise indicated.

EXAMPLE 1
Milk for the Skin, Having Exfoliating Activity

| | |
|---|---|
| 5-n-octanoylsalicylic acid | 0.5% |
| strontium 2,4-pentanedionate | 0.5% |
| BRIJ95 | 2.5% |
| BRIJ92 | 2.5% |
| liquid petroleum jelly | 30% |
| water qs | 100% |

The milk thus formulated was soft, had a good exfoliant property for the skin and did not irritate the skin. It is well suited for use by individuals with sensitive skin.

EXAMPLE 2
Test on Reconstructed Skin

The Episkin system is a model of human epidermis reconstituted in vitro, which was manufactured by the company Episkin. The epidermis contained only one cell type: keratinocytes. The keratinocytes were seeded onto a dermis equivalent which was composed of various types of collagen.

After a period of proliferation of the keratinocytes immersed in the culture medium, the system was raised up to the air/liquid interface. This step of immersing the cultures induced the differentiation of the keratinocytes towards the terminal stage of corneocytes in 13 days, thus allowing the reconstruction, in vitro, of an epidermis which possessed a basal layer, a spiny layer, a granular layer and a horny layer.

The assignee hereof has studied the cytotoxicity of the keratinocytes (3-(4,5-dimethylthiazol-2-yl)-2,5-diphenyltetrazolium bromide test) after applying to this reconstructed skin model various compositions in a proportion of 150 mg/cm$^2$, and maintaining same in an incubator at 37° C./5% $CO_2$ for a period of 18 hours. Each composition was tested on two epidermides of 1.13 cm$^2$.

The basic composition A was:

| | |
|---|---|
| BRIJ95 | 2.5% |
| BRIJ92 | 2.5% |
| liquid petroleum jelly | 30% |
| water qs | 100% | pH = 5.5 ± 0.3

The other compositions tested corresponded to this composition A to which 5-n-octanoylsalicylic acid, alone or in admixture with a compound of formula (I) according to the invention, was added.

The measurement of cell viability was carried out immediately after rinsing of the compositions with phosphate buffered saline (PBS).

Thus, composition A was not cytotoxic. The addition of 0.3% (w/V) of 5-n-octanoylsalicylic acid to this composition rendered it cytotoxic.

The various compositions tested provided the results obtained which are collated in the Table below:

TABLE

| Compound of formula (I) added to composition A | Concentration as % (w/V) of the compound of formula (I) added | Concentration as % (w/V) of the 5-n-octanoyl-salicylic acid added to composition A | % of cell viability |
|---|---|---|---|
| — | 0 | 0.5 | 7.8 |
| Strontium 2,4-pentanedionate | 0.54 | 0.5 | 95.5 |
| Strontium 2,4-pentanedionate | 0.8 | 0.75 | 125.6 |
| Strontium 2,4-pentanedionate | 1.08 | 1 | 113.4 | w/V: weight/volume

The addition of a compound of formula (I) to composition A in the presence of 0.5%, 0.75% or 1% of 5-n-octanoylsalicyclic acid did not render the composition A cytotoxic.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method or regime/regimen for substantially inhibiting, or reducing mammalian skin irritation, comprising topically applying onto the intended or afflicted skin, keratin fibers, nails and/or mucous membranes of a candidate subject in need of such treatment, an anti-irritant effective amount of at least one β-diketone/hydroxylated or carbonated activated cation inorganic/organic complex, wherein said at least one inorganic/organic complex has the formula (I):

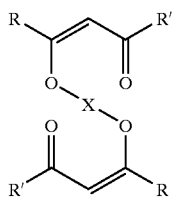

(I)

in which the radicals R, which are identical or different, are each a linear or branched, saturated or unsaturated, optionally hydroxylated alkyl or perfluoroalkyl radical having from 1 to 12 carbon atoms; the radicals R', which are identical or different, are each a linear or branched, saturated or unsaturated, optionally hydroxylated alkyl, alkyloxy or perfluoroalkyl radical having from 1 to 12 carbon atoms; and X is magnesium, strontium, barium, zinc, manganese, palladium or copper.

2. The method or regime/regimen for substantially inhibiting, or reducing mammalian skin irritation as defined by claim 1, wherein said at least one inorganic/organic complex of formula (I) is hydrated or nonhydrated.

3. The method or regime/regimen for substantially inhibiting, or reducing mammalian skin irritation as defined by claim 1, wherein R is a linear or branched, saturated alkyl or perfluoroalkyl radical having from 1 to 6 carbon atoms.

4. The method or regime/regimen for substantially inhibiting, or reducing mammalian skin irritation as defined by claim 1, wherein R' is a linear or branched, saturated alkyl or perfluoroalkyl radical having from 1 to 6 carbon atoms.

5. The method or regime/regimen for substantially inhibiting, or reducing mammalian skin irritation as defined by claim 1, wherein R and R' are linear.

6. The method or regime/regimen for substantially inhibiting, or reducing mammalian skin irritation as defined by claim 1, wherein R and R' are saturated.

7. The method or regime/regimen for substantially inhibiting, or reducing mammalian skin irritation as defined by claim 1, wherein R and R' comprise a difference of at most two carbon atoms with respect to each other.

8. The method or regime/regimen for substantially inhibiting, or reducing mammalian skin irritation as defined by claim 1, wherein X is strontium, copper or zinc.

9. The method or regime/regimen for substantially inhibiting, or reducing mammalian skin irritation as defined by claim 1, wherein R and R' are methyl radicals.

10. A method or regime/regimen for substantially inhibiting, or reducing mammalian skin irritation, comprising applying onto the intended or afflicted skin, keratin fibers, nails and/or mucous membranes of a candidate subject in need of such treatment, an anti-irritant effective amount of at least one inorganic/organic complex from the group consisting of strontium 2,4-pentanedionate, bis(1,1,1,2,2,3,3-heptafluoro-7,7-dimethyl-4,6-octanedionato) strontium hydrate, bis(2,2,6,6-tetramethyl-3,5-heptanedionato)strontium hydrate, strontium hexafluoroacetylacetonate, calcium 2,4-pentanedionate, bis(1,1,1,2,2,3,3-heptafluoro-7,7-dimethyl-4,6-octanedionato) calcium calcium hexafluoroacetylacetonate dihydrate, calcium 2,2,6,6-tetramethyl-3,5-heptanedionate and mixtures thereof.

11. A method or regime/regimen for substantially inhibiting, or reducing mammalian skin irritation, comprising topically applying onto the skin, keratin fibers, nails and/or mucous membranes of a candidate subject in need of such treatment, an irritant amount of at leas one normally skin-irritating active species/product and an anti-irritant effective amount of at least one β-diketone/hydroxylated or carbonated activated cation inorganic/organic complex, wherein said at least one inorganic/organic complex has the formula (I):

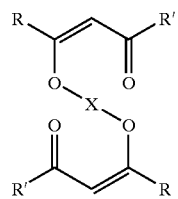

(I)

in which the radicals R, which are identical or different, are each a linear or branched, saturated or unsaturated, optionally hydroxylated alkyl or perfluoroalkyl radical having from 1 to 12 carbon atoms; the radials R', which are identical or different, are each a linear or branched, saturated or unsaturated, optionally hydroxylated alkyl, aklyloxy or perfluoroalkyl radical having from 1 to 12 carbon atoms; and X is magnesium, strontium, barium, zinc, manganese, palladium or copper.

12. The method or regime/regimen for substantially inhibiting, or reducing mammalian skin irritation as defined by claim 11, wherein said at least one inorganic/organic complex of formula (I) is hydrated or nonhydrated.

13. The method or regime/regimen for substantially inhibiting, or reducing mammalian skin irritation as defined by claim 11, wherein said at least one normally skin-irritating active species/product is selected from the group consisting of a preservative, surfactant, fragrance, solvent, propellant, biologically active agent and mixtures thereof.

14. The method or regime/regimen for substantially inhibiting, or reducing mammalian skin irritation as defined by claim 11, wherein said at least one normally skin-irritating active species/product is selected from the group consisting of sunscreen, hydroxy acid, keto acid, retinoid, anthralin, anthranoid, peroxide, minoxidil, lithium salt, antiproliferating agent, vitamin, hair tint, hair dye, perfuming alcoholic solution, antiperspirant, hair-removing active agent, permanent-waving active agent, depigmenting agent, capsaicin, antilouse active agent, ionic detergent agent, nonionic detergent agent, propigmenting agents and mixtures thereof.

15. The method or regime/regimen for substantially inhibiting, or reducing mammalian skin irritation as defined by claim 11, wherein said at least one normally skin-irritating active species/product is selected from the group consisting of an α-hydroxy acid, β-hydroxy acid, an α-keto acid, a β-keto acid, 5-fluorouaracil, methothrexate, vitamin B9, vitamin D or a derivative thereof and mixtures thereof.

16. The method or regime/regimen for substantially inhibiting, or reducing mammalian skin irritation as defined by claim 11, wherein said at least one normally skin-irritating active species/product comprises a β-hydroxy acid.

17. The method or regime/regimen for substantially inhibiting, or reducing mammalian skin irritation as by claim 11, wherein said at least one normally skin/irritating active species/product comprises salicylic acid or a derivative thereof.

18. The method or regime/regimen for substantially inhibiting, or reducing mammalian skin irritation as defined by claim 11, wherein said at least one normally skin-irritating active species/product is selected from the group consisting of 5-n-octanoylsalicylic acid, 5-n-dodecanoylsalicylic acid, a salt thereof and/or ester thereof.

19. A method or regime/regimen for cosmetically improving mammalian skin and/or smoothing facial and/or body skin and/or combating skin aging and/or acne, comprising topically applying onto the intended skin area of a candidate subject in need of such treatment, an effective and anti-irritant amount of at least one inorganic/organic complex having the formula (I):

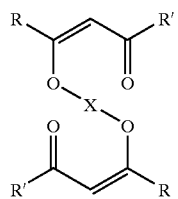
(I)

in which the radicals R, which are identical or different, are each a linear or branched, saturated or unsaturated, optionally hydroxylated alkyl or perfluoroalkyl radical having from 1 to 12 carbon atoms; the radicals R', which are identical or different, are each a linear or branched, saturated or unsaturated, optionally hydroxylated alkyl, alkyloxy or perfluoroalkyl radical having from 1 to 12 carbon atoms; and X is magnesium, strontium, barium, zinc, manganese, palladium or copper.

20. A method or regime/regimen for dermatologically/therapentically combating skin aging and/or reducing wrinkles and fine lines on the skin and/or stimulating epidermal renewal and/or treating acne, comprising topically applying onto the afflicted skin area of a candidate subject in need of such treatment, an effective and anti-irritant amount of at least one inorganic/organic complex having the formal (I):

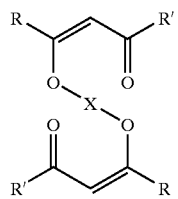
(I)

in which be radicals R, which are identical or different are each a linear or branched, saturated or unsaturated, optionally hydroxylated alkyl or perfluoroalkyl radical having from 1 to 12 carbon atoms; the radicals R', which are identical or different are each a linear or branched, saturated or unsaturated, optionally hydroxylated alkyl alkyloxy or perfluoroalkyl radical having from 1 to 12 carbon atoms; and X is magnesium, strontium, barium, zinc, manganese, palladium or copper.

21. A method or regime/regimen for dermatologically/therapeutically treating shingles, burns, eczema, demodectic acariasis, skin ulcers, fibrosis, psoriasis, pruritus, dermatitis, ichthyosis, corns and/or verrucae afflicting mammalian skin, comprising topically applying onto the afflicted skin area of a candidate subject in need of such treatment, an effective and anti-irritant amount of at least one inorganic/organic complex having the formula (I):

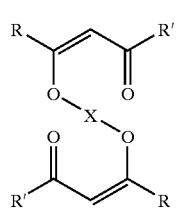
(I)

in which the radical R, which are identical or different, are each a linear or branched saturated or unsaturated, optionally hydroxylated alkyl or perfluoroalkyl radical having from 1 to 12 carbon atoms; the radicals R', which are identical or different, are each a linear or branched, saturated or unsaturated, optionally hydroxylated alkyl, alkyloxy or perfluoroalkyl radical having from 1 to 12 carbon atoms; and X is magnesium, strontium, barium, zinc, manganese, palladium or copper.

22. A method or regime/regimen for treating mammalian skin itching, tautness or stinging, comprising topically applying onto the afflicted skin of a candidate subject in need of such treatment, an anti-irritant effective amount of at least one inorganic/organic complex having the formula (I):

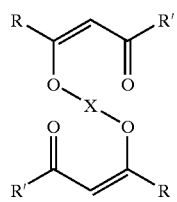
(I)

in which the radicals R, which are identical or different, are each a linear or branched, saturated or unsaturated, optionally hydroxylated alkyl or perfluoroalkyl radical having from 1 to 12 carbon atoms; the radicals R', which are identical or different, are each a linear or branched, saturated or unsaturated, optionally hydroxylated alkyl, alkyloxy or perfluoroalkyl radical having from 1 to 12 carbon atoms; and X is magnesium, strontium, barium, zinc, manganese, palladium or copper.

23. A method or regime/regimen for substantially inhibiting, or reducing the irritation of sensitive mammalian skin, comprising topically applying onto the sensitive skin of a candidate subject in need of such treatment, an anti-irritant effective amount of at least one inorganic/organic complex having the formula (I):

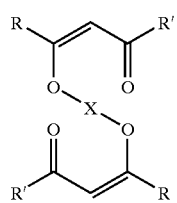
(I)

in which the radicals R, which are identical or different, are each a linear or branched, saturated or unsaturated, optionally hydroxylated alkyl or perfluoroalkyl radical having from 1 to 12 carbon atoms; the radicals R', which are identical or different, are each a linear or branched, saturated or unsaturated, optionally hydroxylated alkyl, alkyloxy or perfluoroalkyl radical having from 1 to 12 carbon atoms; and X is magnesium, strontium, barium, zinc, manganese, palladium or copper.

* * * * *